(12) United States Patent
Chaudhry et al.

(10) Patent No.: US 10,761,095 B2
(45) Date of Patent: Sep. 1, 2020

(54) MICROFLUIDIC DEVICE

(71) Applicant: COMSATS Institute of Information Technology, Islamabad (PK)

(72) Inventors: Madeeha Chaudhry, Islamabad (PK); Malik Abdul Rehman, Islamabad (PK); Raheel Qamar, Islamabad (PK); Arshad Saleem Bhatti, Islamabad (PK)

(73) Assignee: COMSATS Institute of Information Technology, Islamabad (PK)

( * ) Notice: Subject to any disclaimer, the term of this patent is extended or adjusted under 35 U.S.C. 154(b) by 155 days.

(21) Appl. No.: 15/619,096

(22) Filed: Jun. 9, 2017

(65) Prior Publication Data
US 2017/0356924 A1     Dec. 14, 2017

(30) Foreign Application Priority Data
Jun. 9, 2016  (PK) .................................... 339/2016

(51) Int. Cl.
*G01N 33/58*      (2006.01)
*G01N 33/543*     (2006.01)
*B01L 3/00*       (2006.01)

(52) U.S. Cl.
CPC ...... *G01N 33/588* (2013.01); *B01L 3/502715* (2013.01); *B01L 3/502753* (2013.01); *B01L 3/502761* (2013.01); *G01N 33/54346* (2013.01); *G01N 33/54366* (2013.01); *B01L 2300/0867* (2013.01); *B01L 2300/12* (2013.01); *B01L 2300/163* (2013.01)

(58) Field of Classification Search
CPC ......... B01L 2300/0867; B01L 2300/12; B01L 2300/163; B01L 3/502715; B01L 3/502753; B01L 3/502761; G01N 33/54346; G01N 33/54366; G01N 33/588
See application file for complete search history.

(56) References Cited

U.S. PATENT DOCUMENTS

| 6,379,622 | B1 * | 4/2002 | Polak | B82Y 10/00 422/420 |
| 2002/0058273 | A1 * | 5/2002 | Shipwash | B01L 3/5027 435/6.12 |
| 2016/0109467 | A1 * | 4/2016 | Kolb | G01N 33/80 435/7.25 |

* cited by examiner

*Primary Examiner* — Lyle Alexander
*Assistant Examiner* — Bryan Kilpatrick
(74) *Attorney, Agent, or Firm* — H.C. Park & Associates, PLC

(57) ABSTRACT

A microfluidic device including a serum separator, a quantum dot and antibody inlet connected to the serum separator, a quantum dot linked immunosorbent assay (QLISA) chamber connected to the serum separator, and an outlet connected to the QLISA chamber. The microfluidic device is configured to determine an amount of drug in a serum.

15 Claims, 8 Drawing Sheets

MICROFLUIDIC DEVICE

CROSS-REFERENCE TO RELATED APPLICATION

This application claims priority from and the benefit of Pakistani Patent Application No. 339/2016, filed on Jun. 9, 2016, which is hereby incorporated by reference for all purposes as if fully set forth herein.

BACKGROUND

Field

Exemplary embodiments relate to a microfluidic device. In particular, exemplary embodiments relate to a microfluidic device with a quantum dot linked immunosorbent assay (QLISA).

Discussion of the Background

Therapeutic drug monitoring (TDM) is used in assessing drug levels in body fluids to aid in achieving adequate levels of pharmaceutics in patients, to help provide relief, and to prevent further spread of a disease. Pharmacological response of an administered drug depends on factors, such as dosage, absorption, distribution, metabolism, and excretion. For some drugs, clinical assessment is not the only option for ruling out its efficacy. However, for certain drugs, for example digoxin, concentration in the serum plays an important role in efficacy and treatment. Some drugs can be very toxic and may even be fatal at plasma concentration above therapeutic index. Where maintaining a therapeutic plasma concentration is critical for a particular drug, drug level monitoring is critical.

Two techniques are conventionally in use for TDM are chromatography, with or without mass spectroscopy, and immunoassays. Different chromatographic techniques used for drug level monitoring include gas chromatography (GC), ion exchange chromatography (IEC), thin layer chromatography (TLC) and high-performance liquid chromatography (HPLC). However, disadvantages of chromatographic techniques include the requirement of relatively large amounts of sample, a high cost of testing, a laborious laboratory procedure, and a variation in turnaround time from days to weeks. In order to address some of these concerns immunoassays such as radioimmunoassay (RIA) and enzyme linked immunosorbent assay (ELISA) were developed. The RIA and ELISA are relatively quick and are commonly used to detect toxicity associated with drugs. ELISA is the method of choice for therapeutic monitoring of antiepileptic, antiarrhythmics, immunosuppressant, and antibacterial drugs. ELISA is very widely used technique in the field of clinical diagnostics due to high specificity and sensitivity.

Due to use of microfluidics in therapeutic monitoring and dispensation, there is an emerging trend in health care sector for manufacturing of small devices with complex lab procedures and analysis integrated on a microchip. Lab-on-chip is an emerging trend in health care sector involving miniaturization and portability of conventional biological detection setups.

With advancement in microelectromechanical systems (MEMS) technology, miniaturization of ELISA on chip may provide an efficient way for conducting antigen antibody assay coupled with the detection module that can be fluorescence, chemiluminescence, or colorimetric.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments of the present invention provide a microfluidic device targeting point of care diagnosis by performing on chip serum separation and detection of drug levels through an ELISA. In particular, the microfluidic device may include an integrated chip employing a QLISA.

Additional features of the invention will be set forth in the description which follows, and in part will be apparent from the description, or may be learned by practice of the invention.

An exemplary embodiment of the present invention discloses a microfluidic device including a serum separator, a quantum dot and antibody inlet connected to the serum separator, a quantum dot linked immunosorbent assay (QLISA) chamber connected to the serum separator, and an outlet connected to the QLISA chamber. The microfluidic device is configured to determine an amount of drug in a serum.

A length of the microfluidic device may be 55-85 mm.

The serum separator (inlet A) may have a diameter of 7-17 mm.

The QLISA chamber may have a length of 20-40 mm and a width of 5-9 mm.

The outlet may have a diameter of 4-8 mm.

The serum separator may be a first inlet where the sample is injected.

The quantum dot and antibody inlet may be a second inlet (inlet B) configured to receive the injection of fluorescent tags and antibodies against an analytical material.

The fluorescent tags may be gold nanoparticles.

The fluorescent tags may be quantum dots.

A width of a channel connecting the first inlet to the QLISA chamber may be 1-3 mm.

A width of a channel connecting the QLISA chamber to the outlet may be 1-3 mm.

A reaction takes place in the QLISA chamber where laser light falls and emission signal is recorded.

Unbound molecules may be extracted through the outlet.

The first and second inlets and the outlet may be connected to syringes for sample injection and extraction.

The microfluidic device may include materials of silicon and glass.

The microfluidic device may be configured for serum drug level monitoring using non-competitive sandwich enzyme linked immunosorbent assay.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF ILLUSTRATED EMBODIMENTS

Figure 1:
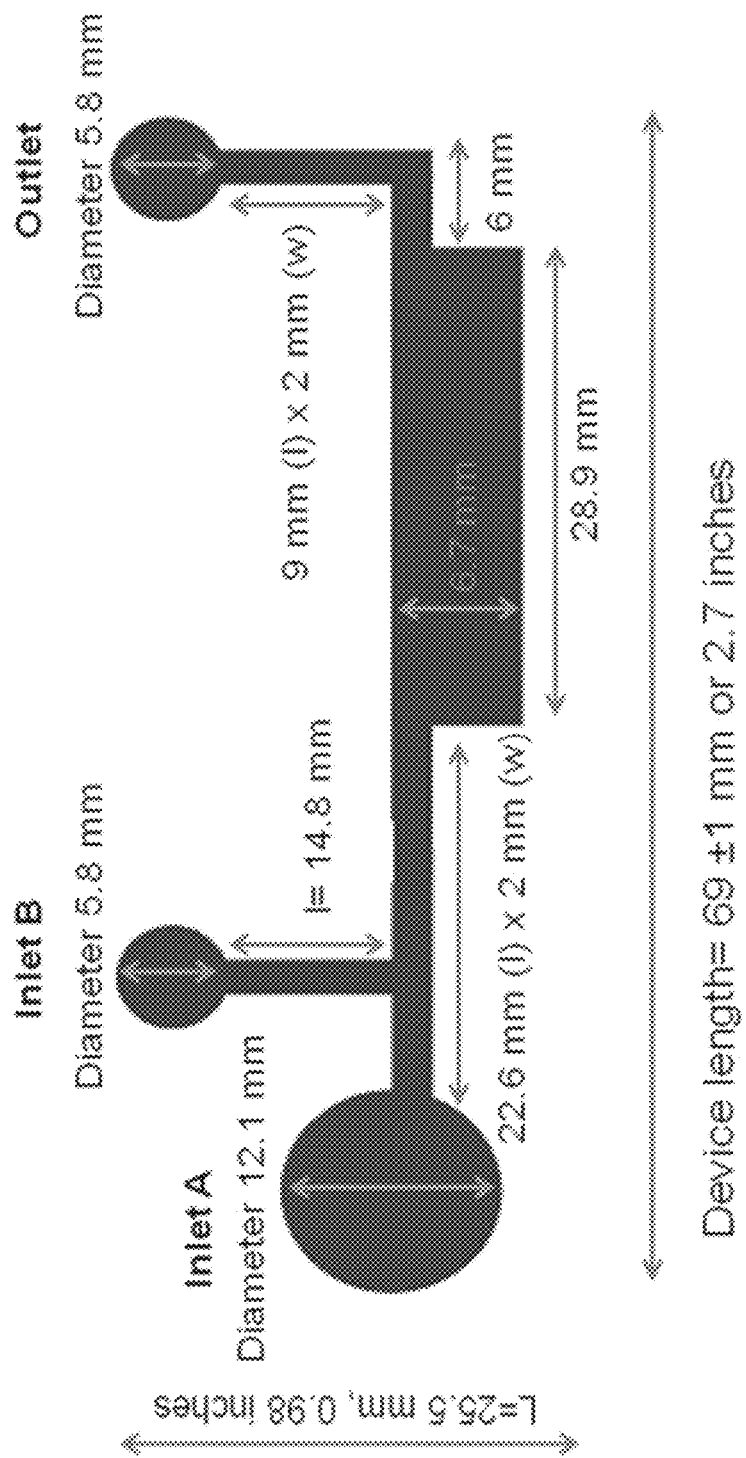
FIG. 1 illustrates a microfluidic device having QLISA according to an exemplary embodiment.

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

Unless otherwise specified, the illustrated exemplary embodiments are to be understood as providing exemplary features of varying detail of various exemplary embodiments. Therefore, unless otherwise specified, the features, components, modules, layers, films, panels, regions, and/or aspects of the various illustrations may be otherwise combined, separated, interchanged, and/or rearranged without departing from the disclosed exemplary embodiments. Further, in the accompanying figures, the size and relative sizes of layers, films, panels, regions, etc., may be exaggerated for clarity and descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

In exemplary embodiments, modules and/or one or more components thereof, may be implemented via one or more general purpose and/or special purpose components, such as one or more discrete circuits, digital signal processing chips, integrated circuits, application specific integrated circuits, microprocessors, processors, programmable arrays, field programmable arrays, instruction set processors, and/or the like.

According to one or more exemplary embodiments, the features, functions, processes, etc., described herein may be implemented via software, hardware (e.g., general processor, digital signal processing (DSP) chip, an application specific integrated circuit (ASIC), field programmable gate arrays (FPGAs), etc.), firmware, or a combination thereof. In this manner, modules and/or one or more components thereof may include or otherwise be associated with one or more memories (not shown) including code (e.g., instructions) configured to cause modules, processors, and/or one or more components thereof to perform one or more of the features, functions, processes, etc., described herein.

FIG. 1 illustrates a microfluidic device having QLISA according to an exemplary embodiment. As shown in FIG. 1, the microfluidic device is fairly small with an elongated shape that has three inputs two inlets on the left and one outlet on the right. Channels to the upper inlet and outlet extend upward and away from the QLISA chamber (main body) of the micro fluidic device at an approximate 90° angle whereas the side inlet has a channel that extends or serum separator away from the QLISA chamber of the microfluidic device at an approximate 0° angle or a 180° angle. The microfluidic has a general overall length with a thicker portion at the QLISA chamber and a narrow portion for the channels.

In an exemplary embodiment, the microfluidic device may have the following dimensions set forth in Table 1.

TABLE 1

Dimensions for the Microfluidic Device

| Device Portion Description | Range | Example Shown in FIG. 1 |
| --- | --- | --- |
| Overall length | 55-85 mm | 69 ± 1 mm |
| Overall width of the main body outside of QLISA chamber | 1-3 mm | 2 mm |
| Length of the QLISA Chamber | 20-40 mm | 28.9 mm |
| Width of the QLISA Chamber | 5-9 mm | 6.7 mm |
| Channel length connecting the QLISA chamber to the outlet | 7-17 mm | 9 mm |
| Channel width connecting the QLISA chamber to the outlet | 1-3 mm | 2 mm |
| Outlet end diameter | 4-8 mm | 5.8 mm |
| Channel length connecting the QLISA chamber to the inlet | 10-20 mm | 14.8 mm |
| Channel width connecting the QLISA chamber to the inlet | 1-3 mm | 2 mm |
| Inlet end diameter (Inlet B) | 4-8 mm | 5.8 mm |
| Serum separator end diameter (Inlet A) | 7-17 mm | 12.1 mm |

As outlined in Table 1, the overall size of the microfluidic device is quite small. It can be 55 mm in length and about 1 mm in width at its most narrow point in the main chamber. The specific example outlined in FIG. 1 illustrates many dimensions and an overall length of 69.5 mm with a narrow width of 2 mm.

Fabrication Method.

Figure 2:
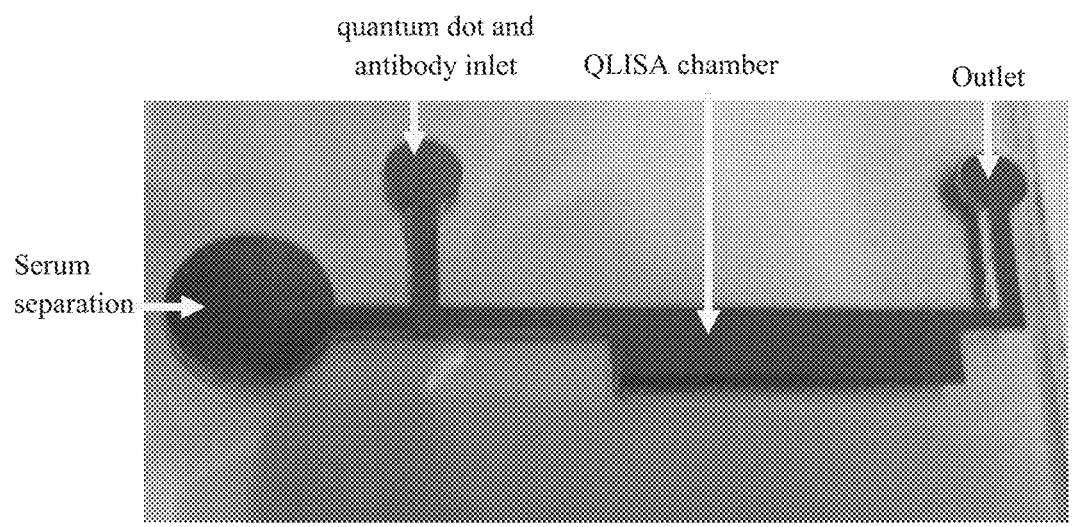
FIG. 2 illustrates a thin film print of device according to an exemplary embodiment.

FIG. 2 illustrates a thin film print of device according to an exemplary embodiment. As shown in FIG. 2, the microfluidic device may be printed using well known thin film printing methods. FIG. 2 shows that that device may have the dimensions discussed above with respect to FIG. 1. Other methods may be used to create the microfluidic device.

Figure 3:
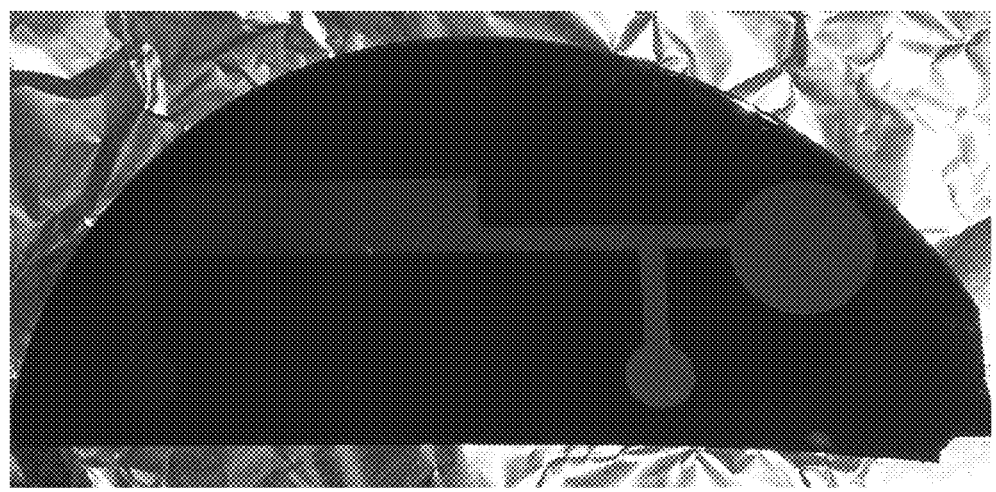
FIG. 3 illustrates a patterned silicon substrate according to an exemplary embodiment.

FIG. 3 illustrates a patterned silicon substrate according to an exemplary embodiment. The method to obtain the illustrated image of FIG. 3 is discussed below.

According to FIG. 3, a wafer cleaning is carried out by ultrasonification of the wafer for approximately 30 minutes in an acetone solution. After 30 minutes of ultrasonification, the mask is dried with liquid nitrogen in a clean environment. Upon drying of the mask, a spin coating of positive photoresist (AZ 40XT) is applied at up to 2000 revolutions per minute for 40 seconds on the mask. The spin coating is followed by pre-bake at 100 Celsius for 10 minutes to evaporate any residual solvent and increase adhesion of mask on the silicon wafer. The pattern from mask is transferred to the silicon wafer using photolithography with Ultraviolet exposure two cycles for 200 seconds. After transfer of pattern to the wafer, the wafer is baked at 200 Celsius for up to two minutes for complete adhesion. Development of the wafer is carried out by immersing the wafer in a developer solution where the positive resist UV exposed area is dissolved in the developer solution. Finally, a hard baking step is carried out to increase the adhesion of pattern on silicon wafer as shown in FIG. 3.

Etching

Figure 4:
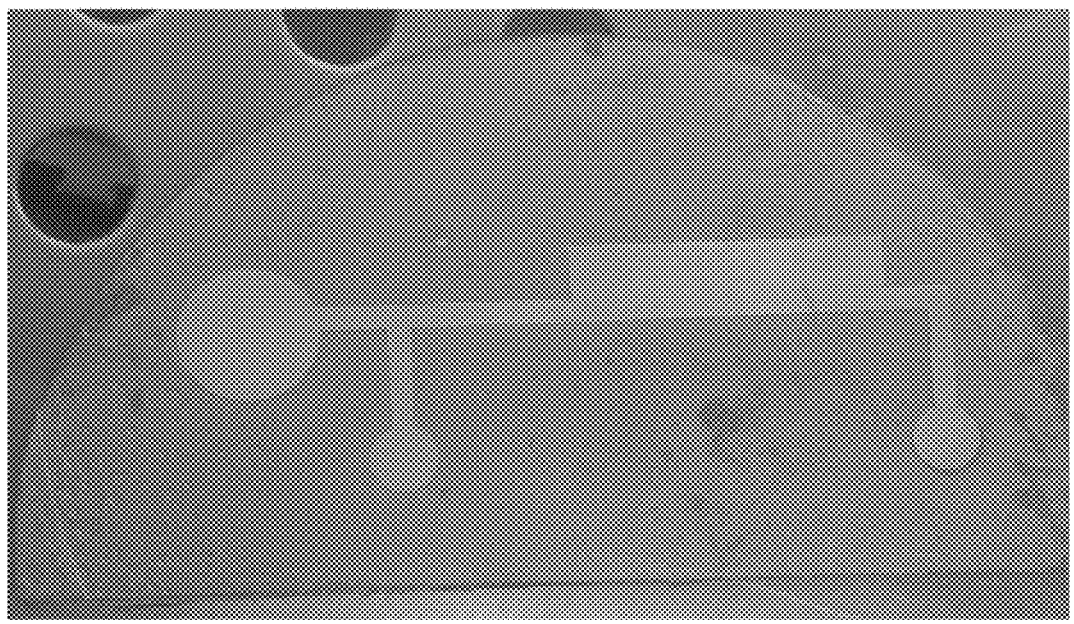
FIG. 4 illustrates an etched silicon substrate according to an exemplary embodiment.
Figure 5:
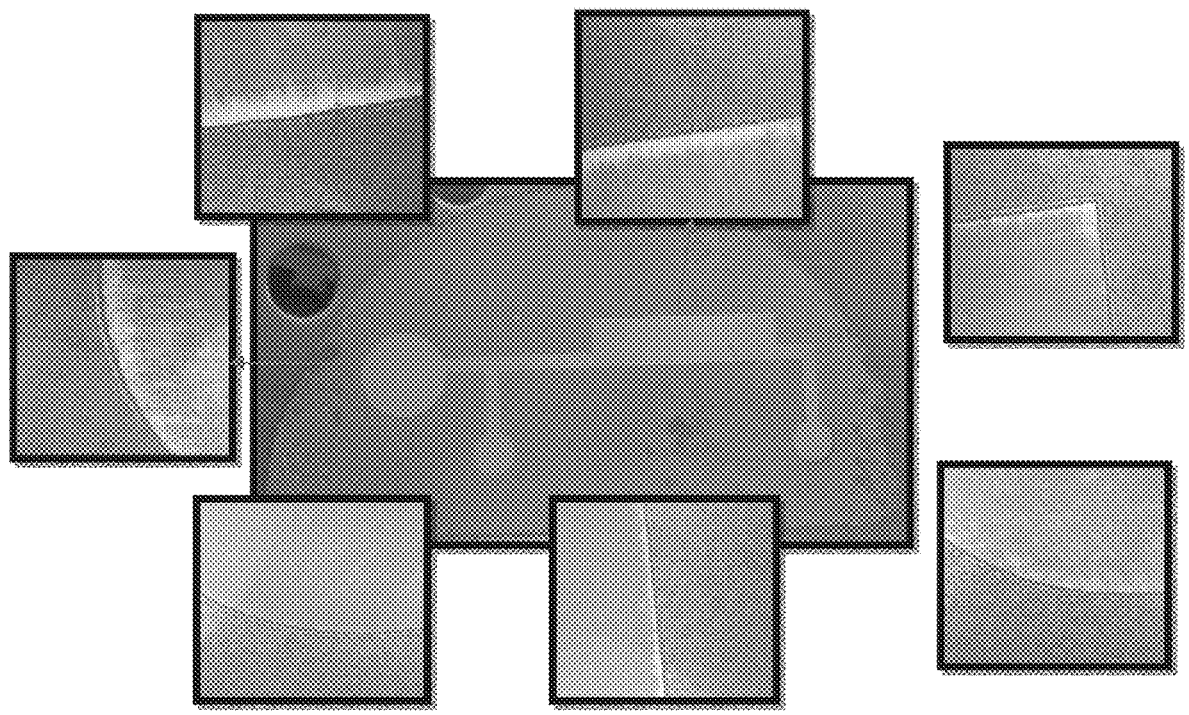
FIG. 5 illustrates an optical microscopy images of the etched silicon according to an exemplary embodiment.

FIG. 4 illustrates an etched silicon substrate according to an exemplary embodiment. FIG. 5 illustrates an optical microscopy images of the etched silicon according to an exemplary embodiment. The method to obtain the illustrated image of FIGS. 4 and 5 are discussed below.

A reactive ion etching of the silicon wafer with patterned device design, according to FIG. 1, is carried out following the hard baking of the silicon wafer. The etching is carried out by using argon and sulfur hexafluoride ($SF_6$) gases and is followed by molding of the QLISA device. The etching is done so that the wafer has an etched pattern with a depth of 70-120 microns.

Mold Formation

For device fabrication polydimethylsiloxane (PDMS) polymer (4 ml, 15:1 ratio of base:curing agent) was poured on clean, etched wafer and was cured at 150° for 1.5 hours. Once the mold is dried completely and hardened on the wafer; it is carefully peeled off using clean tweezers.

The PDMS device mold was bonded to clean glass slide using stamp and stick bonding approach with slight modification (spin coat 0.5 ml at 1500 rpm for 20 s).

The PDMS on glass slide was cured at 60° C.; and after 10 minutes the peeled off device mold is bonded on the glass slide and left to dry for 1 hour at 60-100° C.

Assembly of Completed and Working Device

Figure 6:
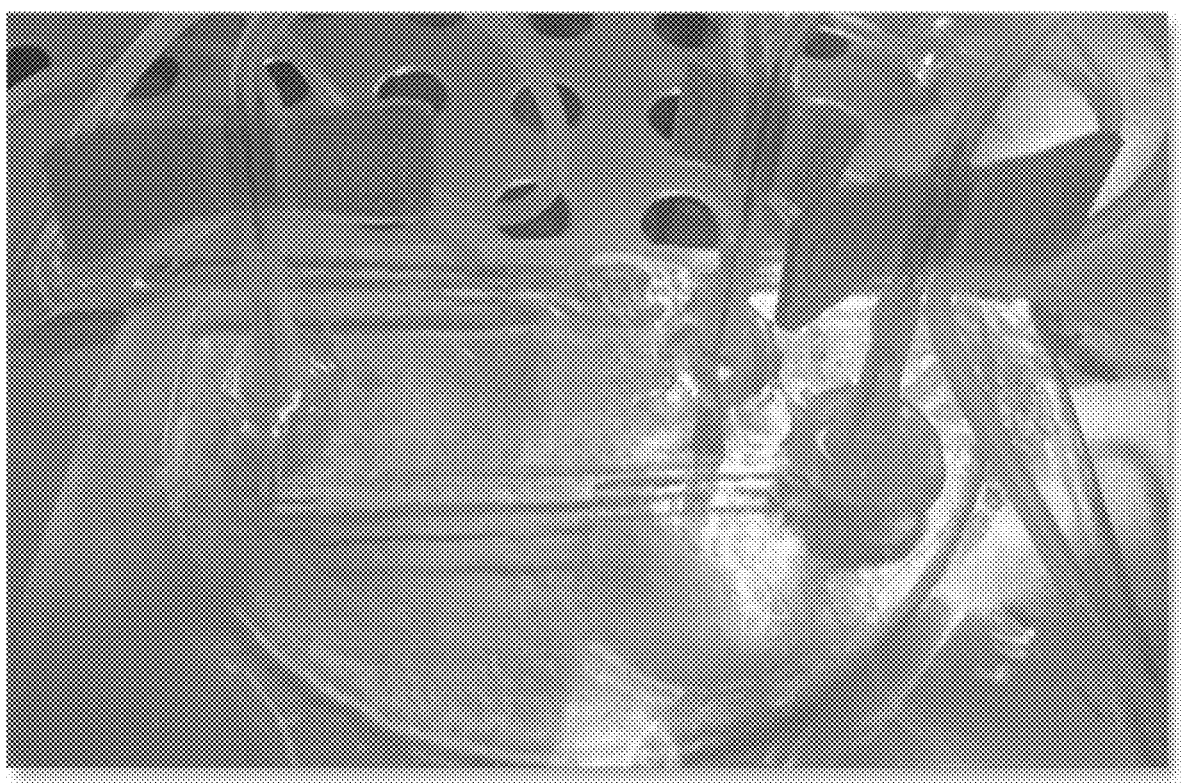
FIG. 6 illustrates an image of a microfluidic device working with inlet and outlet connections according to an exemplary embodiment.

FIG. 6 illustrates an image of a microfluidic device working with inlet and outlet connections according to an exemplary embodiment. This device is described below.

Referring to FIG. 6, the inlet and outlet syringe connections were introduced in the working microfluidic device after the PDMS direct, and perfectly bonded, to the glass slide. The microfluidic device was then assembled in proper portable optical detection setup having laser source, spectrometer, optical fiber, filters and movable stage for sample.

The microfluidic device will perform detection of any biomolecule (drug) depending on the biological technique: sandwich enzyme linked immunoassay with the help of quantum dot instead of biological fluorophores. The detection setup is explained below.

Once a sandwich configuration is completed in the detection chamber/QLIZA chamber that has the primary antibody coated on a surface of glass slide (antibody immobilization), then the primary antibody is conjugated to the biomolecule (drug) followed by conjugation of the biomolecule to a secondary antibody coated on the quantum dot.

During each step of antibody immobilization or biomolecule attachment, glass slide is coated with bovine serum albumin followed by repetitive washing with phosphate buffer saline solution. The purpose of this step is to prevent non-specific adsorption or detection of any other biomolecule except the analytical material of interest in serum sample.

Figure 7A:
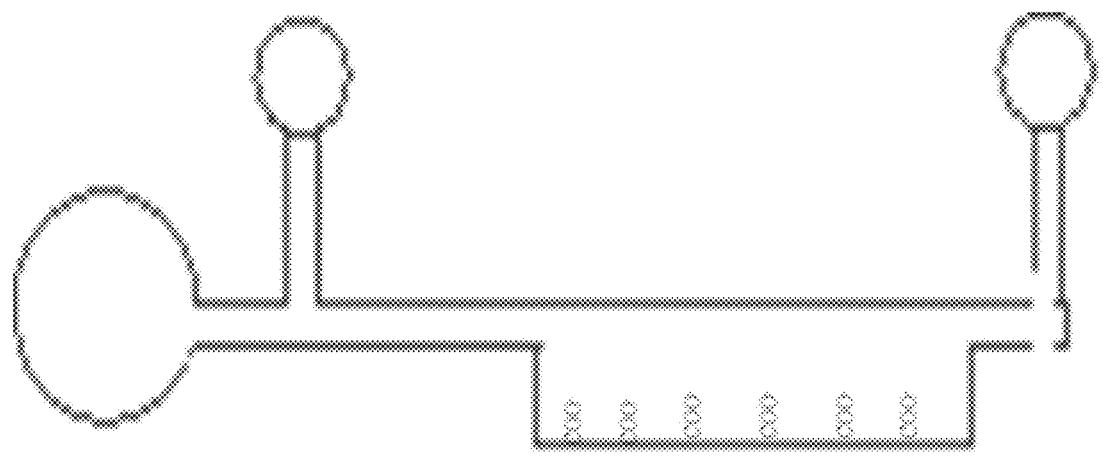
FIG. 7A is a schematic diagram showing the injection and coating of the chamber with a biocompatible material.
Figure 7B:
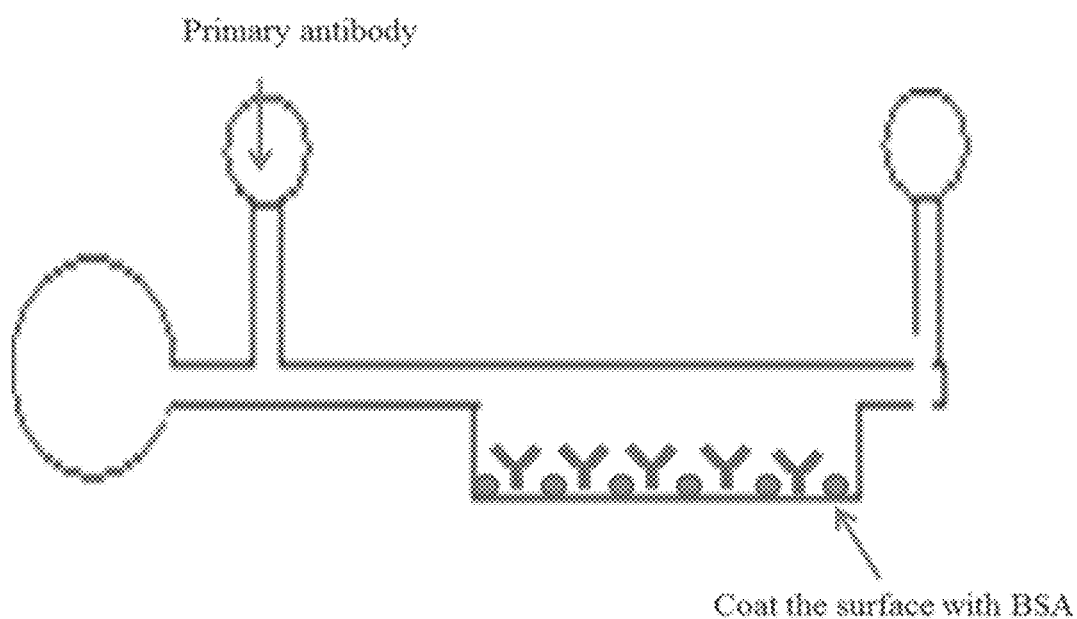
FIG. 7B is a schematic diagram showing the injection and coating of the chamber coated with a primary antibody and bovine serum albumin.
Figure 7C:
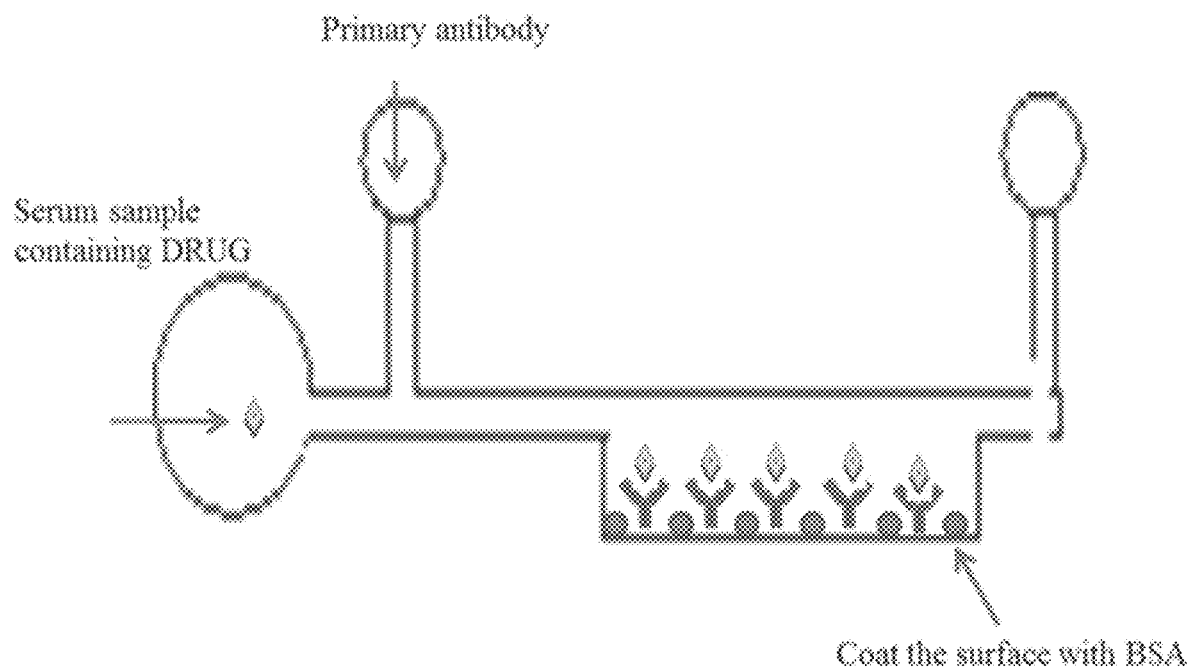
FIG. 7C is a schematic diagram showing the injection of the serum sample of interest.
Figure 7D:
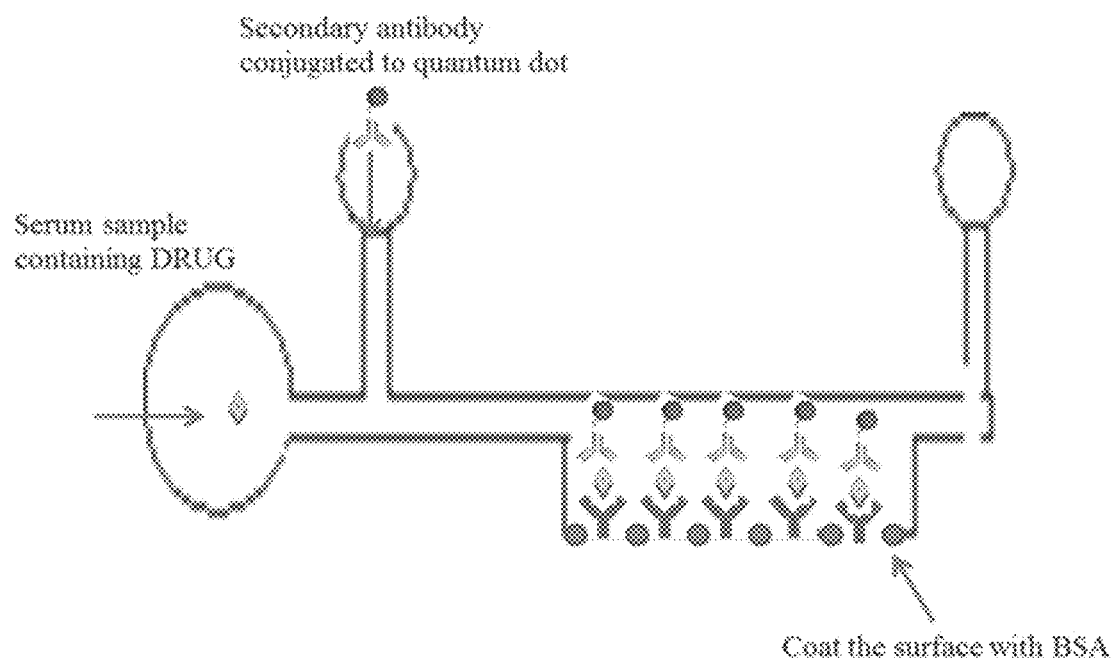
FIG. 7D is a schematic diagram showing the injection of a secondary antibody linked with quantum dots.

FIG. 7A is a schematic diagram showing the injection and coating of the chamber with a biocompatible material. FIG. 7B is a schematic diagram showing the injection and coating of the chamber coated with a primary antibody and bovine serum albumin. FIG. 7C is a schematic diagram showing the injection of the serum sample of interest. FIG. 7D is a schematic diagram showing the injection of a secondary antibody linked with quantum dots. These figures are discussed below.

As shown in FIG. 7A, the PDMS based device is coated with any biocompatible material to prevent sticking of biomolecules to the walls of PDMS. The QLIZA chamber is first activated with carboxyl group for antibody immobilization using carbodiimide crosslinking chemistry.

As shown in FIG. 7B, the chamber is then coated with primary antibody (50 µl, 0.001 dilution in PBS buffer) by injecting the primary antibody through a second inlet.

The chamber is then washed with phosphate buffer saline (PBS) solution to remove any unbound antibody from the chamber.

Referring to FIG. 7B, Bovine serum albumin (BSA) (50 µl, 0.1% solution) is then injected to coat the unbound glass surfaces in order to prevent any non-specific adsorption or detection of irrelevant analytical material in serum.

As shown in FIG. 7C, serum sample containing analytical material of interest (drug) (50 µl, 0.8 ng/ml) is injected from the first inlet. The serum sample then binds to available primary antibody sites in the QLIZA chamber.

The device is again washed with PBS buffer solution to remove any unbound analytical material form the chamber, to prevent non-specific detection.

As shown in FIG. 7D, the secondary antibody (50 µl, 0.001 dilution in PBS) linked with quantum dots (1 mg, 500 µl) is injected in the second inlet. The secondary antibody will bind to the available antigen binding sites.

PBS washing step is preformed again to remove unbound antibodies from the chamber.

Now the device with the sample is ready for detection.

The sample may be placed in a proper sample holder in the optical setup and excited with a laser light of wavelength 404 nm. The emitted light from the sample is collected by a collimating lens which aligns the emitted light rays. The lens is connected to optical fiber, which transmits light collected from the collimating lens to spectrometer.

The spectrometer, connected to computer, displays the results in from of an emission spectra. The changes in the intensity of emitted light are helpful in detection or assessing the level of any biomolecule in serum.

Figure 8A:
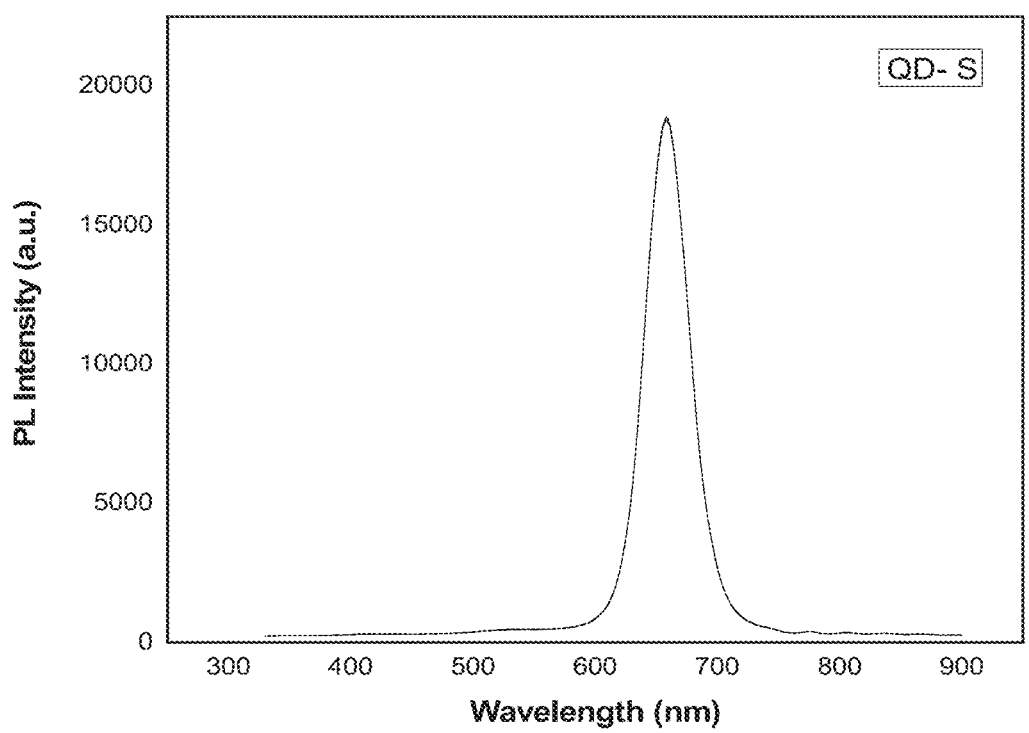
FIG. 8A is a graph showing the photoluminescence of quantum dots dispersed in chloroform.
Figure 8B:
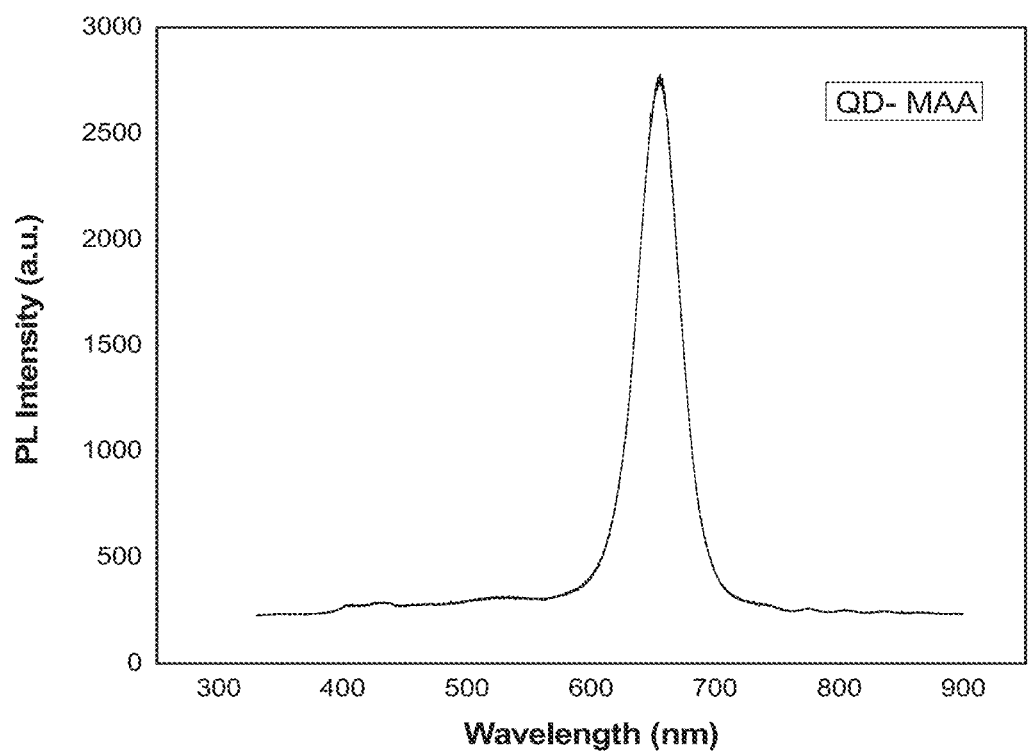
FIG. 8B is a graph showing the photoluminescence of mercaptoacetic acid coated quantum dots in water.
Figure 8C:
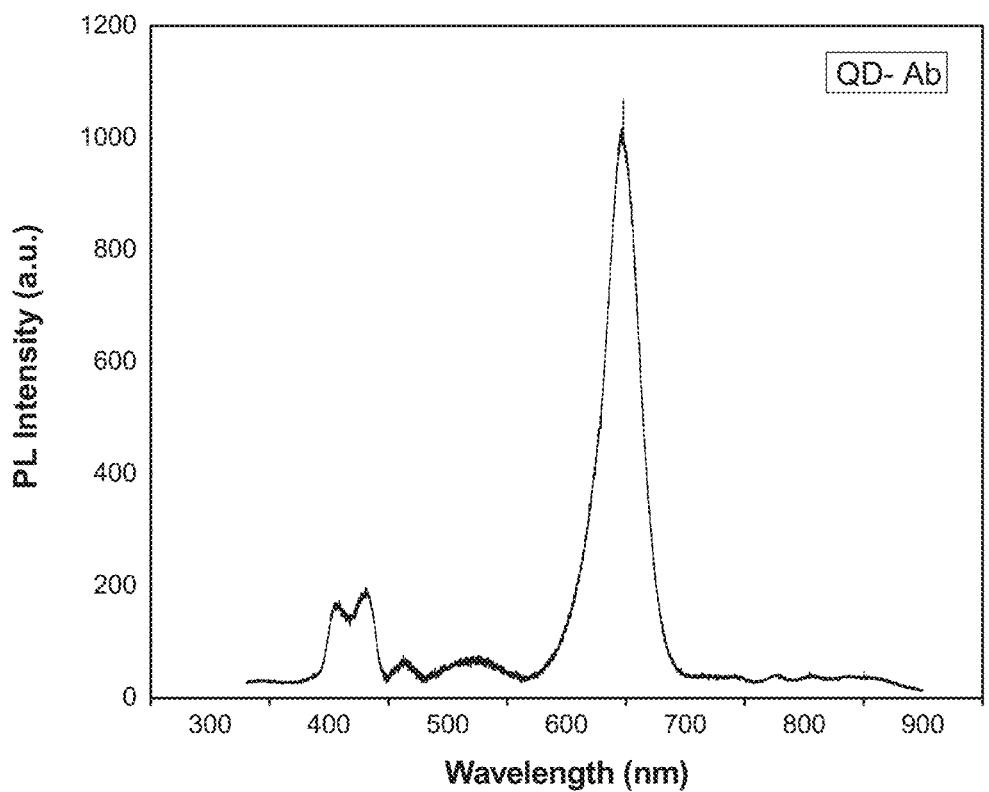
FIG. 8C is a graph showing the photoluminescence of antibody coated quantum dots in water.
Figure 8D:
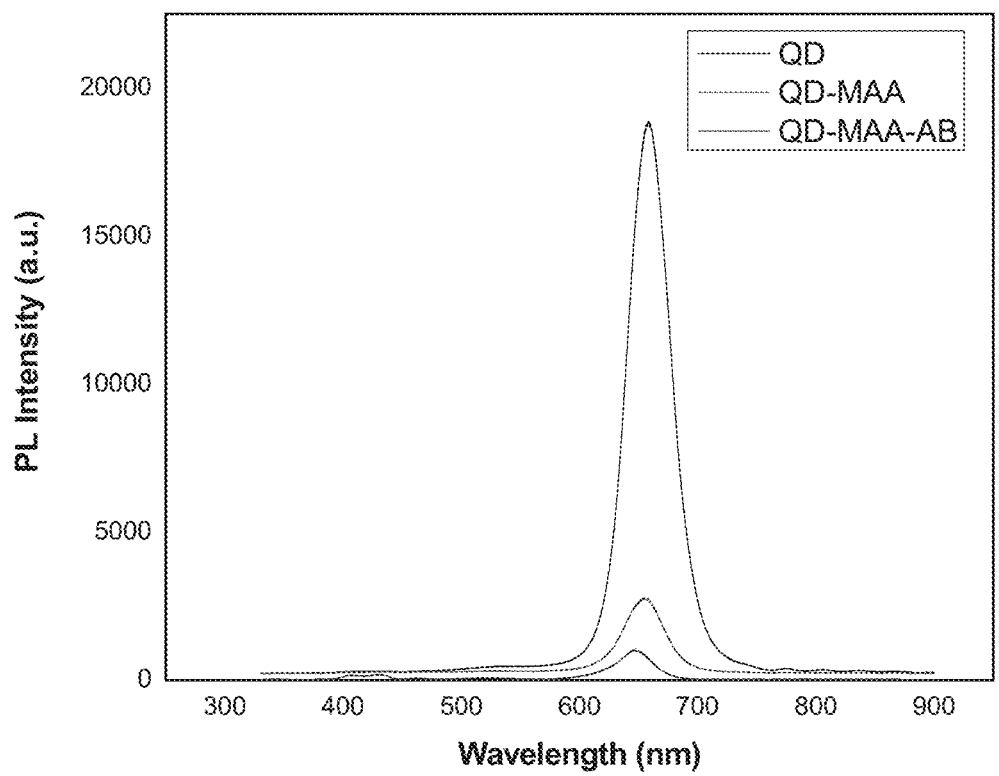
FIG. 8D is a graph showing a comparison of the graphs of FIGS. 8A, 8B, and 8C.

FIG. 8A is a graph showing the photoluminescence of quantum dots dispersed in chloroform. FIG. 8B is a graph showing the photoluminescence of mercaptoacetic acid coated quantum dots in water. FIG. 8C is a graph showing the photoluminescence of antibody coated quantum dots in water. FIG. 8D is a graph showing a comparison of the graphs of FIGS. 8A, 8B, and 8C. These figures are discussed below.

To monitor the change in emission intensity of dots before and after biofunctionalization of the quantum dots (QDs) photoluminescence (PL) spectra were acquired using the detection system described earlier.

FIG. 8A shows the PL spectra of QDs dispersed in chloroform with emission wavelength of 665 nm.

In order to make QDs water soluble (as they are soluble in chloroform) and for antibody conjugation, the surface of QDs were coated with mercaptoacetic acid (MAA). The MAA acts as a linker with thiol at a first end and carboxyl group at a second end. At the first end, sulfur will bind with the QDs sulfur (CdSe/ZnS) through S—S bond. The carboxyl end (second end) of MAA renders the QDs water soluble.

FIG. 8B shows a decrease in emission intensity of dots with a blue shift of 650 nm after coating with MAA or in water when compared to chloroform.

After making the dots water soluble, next step is conjugation of an antibody. Using carbodiimide chemistry, a carboxyl group of QDs will bind with the antibody amine group through C—N bond as shown in FIG. 8C. The PL spectra of MAA QDs with an antibody dispersed in water is 645 nm.

The comparison of change in emission of dots after coating with MAA and finally with an antibody is shown in FIG. 8D.

Proposed detection scheme:

Conventional therapeutic level of detection of digoxin drug is 0.8 ng-2.0 ng per ml.

With said device the detection methodology would involve detection of different concentrations of drug spiked in PBS and then in serum from 0.1 ng to 1 μg including the therapeutic range of 0.8 ng-2.0 ng per ml.

Another set of experiment would run in parallel as confirmation of results. Acquiring the spectra of chamber/glass surface after coating with primary antibody, then with drug immobilized on the primary antibody (blank spectra) followed by final spectra with secondary antibody immobilized.

The limit of detection (LOD) achievable with the said device is to be about 0.1 ng per ml. Experiments of quantum dot conjugation with antibody and detection using the said optical setup has been completed FIG. 8A-8C.

The said device is portable, reusable and produce results within 30 minutes as compared to time consuming and laborious procedures in conventional machine.

What is claimed is:

1. A microfluidic device, consisting of:
a first channel;
a serum separator disposed at a first end of the first channel and comprising a first inlet configured for sample injection and an outlet connected to the first end of the first channel;
a quantum dot and antibody inlet connected to an intermediate portion of the first channel via an inlet channel;
a quantum dot linked immunosorbent assay (QLISA) chamber comprising an inlet connected to a second end of the first channel, an integrated chip including the QLISA disposed in the QLISA chamber, and an outlet;
a second channel comprising a first end connected to the outlet of the QLISA chamber; and
an outlet connected to a second end of the second channel, wherein the microfluidic device is configured to determine an amount of drug in a serum.

2. The device of claim 1, wherein a length of the microfluidic device is 55-85 mm.

3. The device of claim 1, wherein the serum separator has a diameter of 7-17 mm.

4. The device of claim 1, wherein the QLISA chamber has a length of 20-40 mm and a width of 5-9 mm.

5. The device of claim 1, wherein the outlet has a diameter of 4-8 mm.

6. The device of claim 1, wherein the quantum dot and antibody inlet comprises a second inlet configured to receive an injection of fluorescent tags and antibodies against an analytical material.

7. The device of claim 6, wherein the fluorescent tags are gold nanoparticles.

8. The device of claim 6, wherein the fluorescent tags are quantum dots.

9. The device of claim 1, wherein a width of the first channel is 1-3 mm.

10. The device of claim 1, wherein a width of the second channel connecting the QLISA chamber to the outlet is 1-3 mm.

11. The device of claim 1, wherein a reaction takes place in the QLISA chamber where laser light falls and emission signal is recorded.

12. The device of claim 1, wherein unbound molecules are extracted through the outlet.

13. The device of claim 6, wherein the first and second inlets and the outlet consist of syringe connections configured to be connected to syringes for sample injection and extraction.

14. The device of claim 1, wherein the microfluidic device is formed of silicon and glass.

15. The device of claim 1, wherein the device is configured for serum drug level monitoring using non-competitive sandwich enzyme linked immunosorbent assay.

* * * * *